(12) United States Patent
Freeman et al.

(10) Patent No.: US 11,648,018 B2
(45) Date of Patent: *May 16, 2023

(54) ORTHOPAEDIC SURGICAL INSTRUMENT

(71) Applicant: DePuy Ireland Unlimited Company, Ringaskiddy (IE)

(72) Inventors: Robert Freeman, Leeds (GB); Kevin D. Booth, Leeds (GB); Mark Reason, Leeds (GB); Duncan J. Beedall, Leeds (GB); Michael J. Rees, Leeds (GB); Alberto P. Verteramo, Turin (IT)

(73) Assignee: DePuy Ireland Unlimited Company, Ringaskiddy (IE)

( * ) Notice: Subject to any disclaimer, the term of this patent is extended or adjusted under 35 U.S.C. 154(b) by 328 days.

This patent is subject to a terminal disclaimer.

(21) Appl. No.: 17/122,098

(22) Filed: Dec. 15, 2020

(65) Prior Publication Data
US 2021/0093334 A1 Apr. 1, 2021

Related U.S. Application Data

(63) Continuation of application No. 16/213,609, filed on Dec. 7, 2018, now Pat. No. 10,863,996.

(60) Provisional application No. 62/596,257, filed on Dec. 8, 2017.

(51) Int. Cl.
| | | |
|---|---|---|
| A61B 17/17 | (2006.01) | |
| A61B 17/15 | (2006.01) | |
| A61B 17/16 | (2006.01) | |
| A61F 2/46 | (2006.01) | |
| A61B 17/72 | (2006.01) | |

(52) U.S. Cl.
CPC ........ *A61B 17/1764* (2013.01); *A61B 17/154* (2013.01); *A61B 17/155* (2013.01); *A61B 17/1615* (2013.01); *A61B 17/1675* (2013.01); *A61F 2/461* (2013.01); *A61B 17/164* (2013.01); *A61B 17/72* (2013.01)

(58) Field of Classification Search
CPC . A61B 17/154; A61B 17/155; A61B 17/1615; A61B 17/1675; A61B 17/1764; A61B 17/164; A61B 17/72; A61F 2/461
See application file for complete search history.

(56) References Cited

U.S. PATENT DOCUMENTS

| | | |
|---|---|---|
| 5,681,316 A | 10/1997 | DeOrio et al. |
| 6,013,081 A | 1/2000 | Burkinshaw et al. |
| 8,814,874 B2 | 8/2014 | Hunter et al. |
| 10,863,996 B2 | 12/2020 | Freeman et al. |

(Continued)

FOREIGN PATENT DOCUMENTS

| | | |
|---|---|---|
| RU | 2332181 C2 | 8/2008 |
| WO | 2009006741 A1 | 1/2009 |

OTHER PUBLICATIONS

Partial European Search Report for European International Application No. PCT/EP2018/083972, dated Mar. 18, 2019, 11 pages.

(Continued)

*Primary Examiner* — Samuel S Hanna
(74) *Attorney, Agent, or Firm* — Barnes & Thornburg LLP

(57) ABSTRACT

An orthopaedic surgical instrument for use in resecting a patient's bone is disclosed. In some embodiments, the instrument may be for single patient use and may be disposed of at the end of each surgical procedure.

6 Claims, 16 Drawing Sheets

(56) References Cited

U.S. PATENT DOCUMENTS

| | | |
|---|---|---|
| 2006/0122618 A1 | 6/2006 | Claypool et al. |
| 2009/0006741 A1 | 1/2009 | Lubbers et al. |
| 2010/0121334 A1 | 5/2010 | Couture et al. |
| 2013/0317501 A1* | 11/2013 | Booth .................... A61B 17/72 |
| | | 606/62 |

OTHER PUBLICATIONS

Russia Search Report for Russia Application No. 2020122400/14, dated Dec. 6, 2021, 2 pages.

* cited by examiner

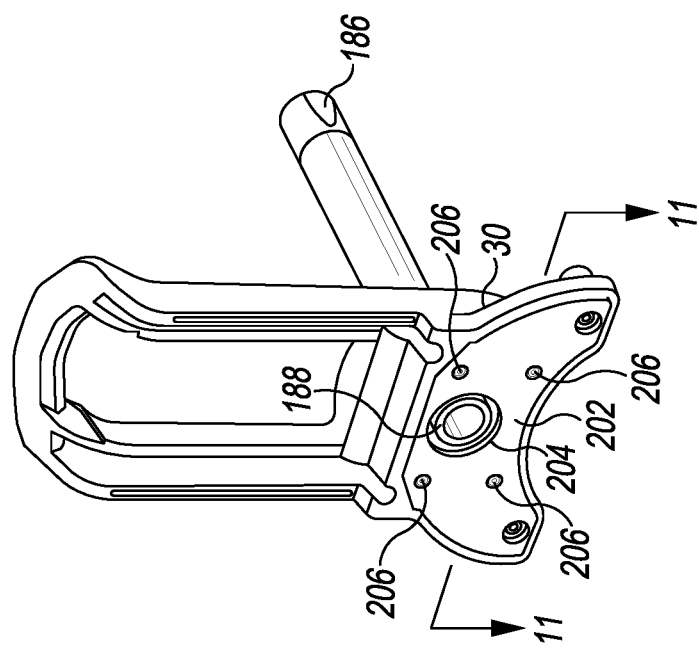
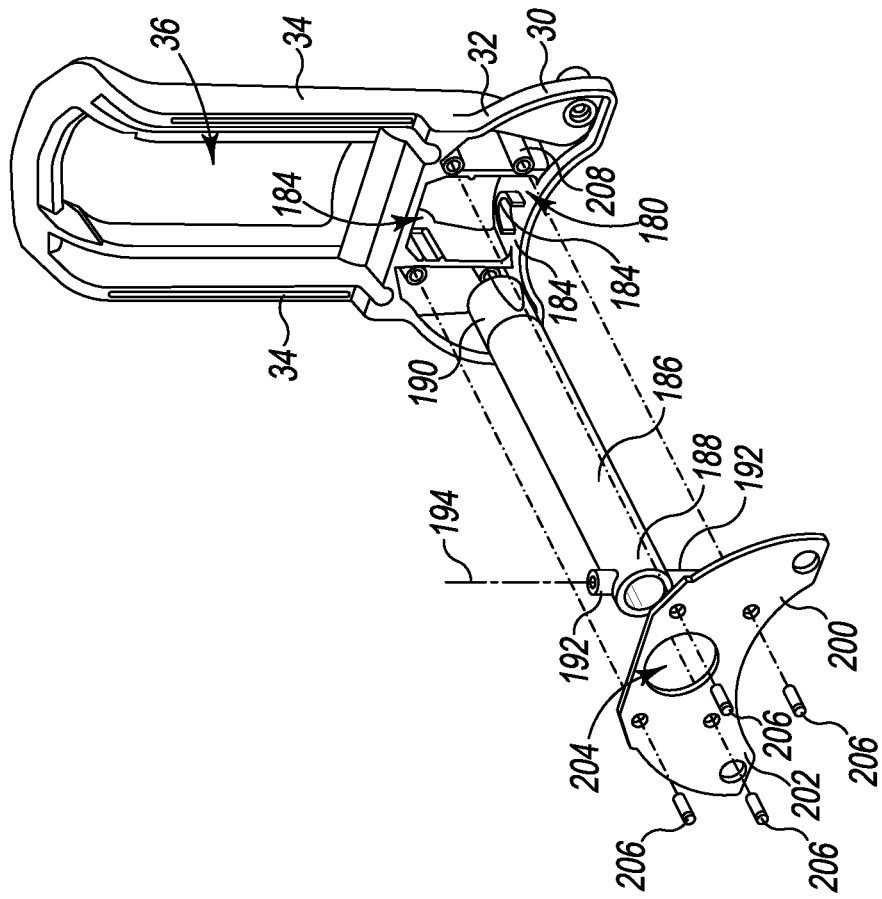
Fig. 10
Fig. 9

ORTHOPAEDIC SURGICAL INSTRUMENT

This application is a continuation of U.S. patent application Ser. No. 16/213,609, now U.S. Pat. No. 10,863,996, which was filed on Dec. 7, 2018 and claims priority under 35 U.S.C. § 119 to U.S. Patent App. Ser. No. 62/596,257, which was filed on Dec. 8, 2017. The entirety of both of the above-identified applications is expressly incorporated herein by reference.

TECHNICAL FIELD

The present disclosure relates generally to orthopaedic instruments for use in the performance of an orthopaedic joint replacement procedure, and, more particularly, to orthopaedic surgical instruments for use in the performance of a knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes multiple prosthetic components, including a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur.

During any knee surgery, the orthopaedic surgeon typically uses a variety of different orthopaedic surgical instruments such as, for example, cutting blocks, reamers, drill guides, and other surgical instruments to prepare the patient's bones to receive the knee prosthesis.

SUMMARY

According to one aspect of the disclosure, an orthopaedic surgical instrument for use in resecting an end of a patient's bone is disclosed. In some embodiments, the instrument may be for single patient use and may be disposed of at the end of each surgical procedure.

In some embodiments, the instrument may house a vargus/valgus pivot mechanism, which is maintained in position by a datum/distal plate that clamps the pivot pins with sufficient force to allow rotation but maintain alignment of the pivot pins and thus the distal resection plate with an intramedullary rod. The instrument includes a housing, an elongated pivot tube, a steel datum/distal plate, and a number of screws (e.g., 4) that are assembled to a specified torque to ensure function and accuracy of the device.

To allow for varying patient anatomy and femoral sizes, the instrument also includes in some embodiments a translation mechanism that permits the cutting block to slide anteriorly/posteriorly (in use, inferiorly/superiorly) relative to the patient's bone. In that way, the cutting block may be moved into contact with the patient's anterior bone to allow it to be pinned in position and form a stable platform to perform the resection. According to one aspect, two bodies are used on either side of at least one arm of the instrument housing. The two bodies may be clamped together using a threaded section with sufficient torque to ensure accuracy and still permit sliding. To reduce friction and also allow for an adjustable surface to ensure accuracy, raised ribs may be present on each arm.

In some embodiments, the translation mechanism may include a primary and secondary locking ring. The primary locking ring lock secures the parts together firmly to ensure accuracy while permitting the cutting block to slide. It may be assembled via a bespoke socket and set to a prescribed torque. The secondary ring acts to lock the primary ring in place to retain the primary ring in position and prevent an angular departure of the translation mechanism (and hence the cutting block) from the bone-engaging surface of the instrument. It may also be assembled via a bespoke socket and set to a prescribed torque.

The instrument may also include a distal resection/height adjustment mechanism. In some embodiments, the mechanism may include a mounting bracket with a double start threaded helix and an adjustment control knob. In some embodiments, the mechanism may sit within the translation mechanism. The threaded helix may run within the control knob and may be used to actuate the height adjustment mechanism. To provide a basis from which to actuate, the control knob may snap into place on the translation mechanism. Prior to assembly, the knob may be correctly indexed and then snapped into place, thereby ensuring that the numbers printed on the knob, match the resection settings.

According to another aspect of the disclosure, an orthopaedic surgical instrument comprising a cutting block including a cutting slot sized to receive a cutting tool to guide a resection of a patient's bone is disclosed. The orthopaedic surgical instrument also comprises a housing coupled to the cutting block, and the housing includes a central slot and a pair of brackets positioned on opposite sides of the central slot. A distal plate is coupled to the housing, and the distal plate includes a bone-engaging surface and an opening that is defined in the bone-engaging surface and is aligned with the central slot. The orthopaedic surgical instrument also comprises an elongated shaft extending from a first end positioned in the central slot, a pair of pivot pins coupled to the elongated shaft, each pivot pin being positioned in one of the pair of brackets, and an intramedullary rod configured to be inserted into a medullary canal of the patient's bone. The intramedullary rod extends through the elongated shaft and the opening defined in the distal plate to define a longitudinal axis that extends transverse to the bone-engaging surface of the distal plate. The bone-engaging surface extends generally parallel to the cutting slot of the cutting block, and the pivot pins cooperate to define a pivot axis about which the elongated shaft and the intramedullary rod are configured to pivot relative to the distal plate to change a magnitude of an angle defined between the longitudinal axis and the bone-engaging surface of the distal plate. In some embodiments, the distal plate may engage the pivot pins to retain the pivot pins in the brackets of the housing.

In some embodiments, the distal plate may be formed from a metallic material, and the pivot pins may be formed from a plastic material. In some embodiments, the orthopaedic surgical instrument may further comprise a number of fasteners that secure the distal plate to the housing to clamp the pivot pins between inner walls of the brackets and the distal plate. Additionally, in some embodiments, the pivot pins may be clamped between distal-facing inner walls of the brackets and a proximal-facing surface of the distal plate.

In some embodiments, each bracket may include the distal-facing inner wall and a pair of side inner walls that cooperate with the distal-facing inner wall to define an open-ended channel sized to receive one of the pivot pins, and each pivot pin may extend outwardly from the open-ended channel of its corresponding bracket. Additionally, in some embodiments, the distal plate may include a bowed central section that engages the pivot pins extending outwardly from the open-ended channels of the brackets.

According to another aspect, an orthopaedic surgical instrument comprises an intramedullary rod configured to be inserted into a medullary canal of a patient's bone and a housing coupled to the intramedullary rod. The housing includes a pair of arms spaced apart to define an elongated slot, and each arm includes a first longitudinal rib formed on a proximal surface and a second longitudinal rib formed on a distal surface positioned opposite the proximal surface. The orthopaedic surgical instrument also comprises a translation frame configured to slide along the pair of arms.

The translation frame comprises a first body including a central section positioned in the elongated slot of the housing and a pair of first flanges extending outwardly from the central section. Each first flange includes a proximal surface that engages the first longitudinal rib of one of the pair of arms. The translation frame also comprises a second body coupled to the first body. The second body includes a pair of second flanges, and each second flange includes a distal surface that engages the second longitudinal rib of one of the pair of arms to couple the first body and the second body to the housing. A mounting bracket is coupled to the first body and the second body, and a cutting block is coupled to the mounting bracket such that the cutting block is configured to slide with the translation frame. The cutting block includes a cutting slot sized to receive a cutting tool to guide a resection of the patient's bone.

In some embodiments, a pocket may be defined in the proximal surface of each first flange to create a relief section in the proximal surface. Additionally, in some embodiments, a pocket may be defined in the distal surface of each second flange to create a relief section in the distal surface.

In some embodiments, each longitudinal rib may include a curved outer surface.

In some embodiments, the second body may include a base plate and an elongated shaft that extends outwardly from the base plate through the central section of the first body. The translation frame may further comprise a fastener secured to the elongated shaft of the second body to couple the second body to the first body. Additionally, in some embodiments, the elongated shaft of the second body may include a threaded outer surface, and the fastener may include a locking ring that is threaded onto the elongated shaft.

In some embodiments, the locking ring may be a first locking ring, and the fastener may include a second locking ring that is threaded onto the elongated shaft to retain the first locking ring in position on the elongated shaft.

In some embodiments, the housing and the components of the translation frame may be formed from a plastic material.

In some embodiments, the housing may further include a central slot that is spaced apart from the elongated slot and a pair of brackets positioned on opposite sides of the central slot. Additionally, in some embodiments, the orthopaedic surgical instrument may include a distal plate coupled to the housing that includes a bone-engaging surface and an opening that is defined in the bone-engaging surface and is aligned with the central slot, an elongated shaft extending from a first end positioned in the central slot, and a pair of pivot pins coupled to the elongated shaft, each pivot pin being positioned in one of the pair of brackets. The intramedullary rod may extend through the elongated shaft and the opening defined in the distal plate and define a longitudinal axis that extends transverse to the bone-engaging surface of the distal plate. The bone-engaging surface may extend generally parallel to the cutting slot of the cutting block, and the pivot pins may cooperate to define a pivot axis about which the elongated shaft and the intramedullary rod are configured to pivot relative to the distal plate to change a magnitude of an angle defined between the longitudinal axis and the bone-engaging surface of the distal plate. In some embodiments, the distal plate may engage the pivot pins to retain the pivot pins in the brackets of the housing.

According to another aspect, an orthopaedic surgical instrument comprises an intramedullary rod configured to be inserted into a medullary canal of a patient's bone and a frame coupled to the intramedullary rod, The frame includes a base plate, an elongated shaft that extends outwardly from the base plate, and a first annular groove formed on an outer surface of the elongated shaft. The orthopaedic surgical instrument further comprises a mounting bracket including a main body positioned on one side of the base plate of the frame and a threaded rod coupled to the main body and extending outwardly along a longitudinal axis from a passageway defined in the elongated shaft, a cutting block coupled to the mounting bracket, the cutting block including a cutting slot sized to receive a cutting tool to guide a resection of the patient's bone, and a control knob positioned over a distal tip of the threaded rod of the mounting bracket. The control knob is rotatable about the longitudinal axis to adjust an adjustment distance between the cutting slot of the cutting block and the base plate of the frame. The threaded rod extends into an aperture of the control knob that is defined by an inner wall of the control knob, and the threaded rod engages a threaded hub within the aperture to couple the mounting bracket to the control knob. A second annular rib is formed on the inner wall of the control knob, which engages the first annular groove of the frame to secure the control knob and the mounting bracket to the frame.

In some embodiments, the control knob may include a plurality of visual indicators corresponding to a plurality of different adjustment distances between the cutting slot of the cutting block and the main body of the mounting bracket, and the frame may include an alignment guide configured to be aligned with a first visual indicator of the plurality of visual indicators of the control knob to index the control knob to a first adjustment distance.

In some embodiments, a first tab may extend outwardly from the hub of the control knob. The frame may include a second tab configured to engage the first tab at a first rotational position of the control knob and at a second rotational position of the control knob. An angle may be defined between the first rotational position and the second rotational position. In such embodiments, the angle defines the maximum rotation of the control knob about the longitudinal axis.

In some embodiments, the frame may include an inner wall that defines the passageway and a plurality of ribs that are formed on the inner wall, the mounting bracket may include an elongated body that extends outwardly from the main body to a distal end, and the threaded rod extends outwardly from the distal end to its distal tip, and the elongated body may include a pair of planar surfaces that engage the plurality of ribs to prevent rotation of the mounting bracket about the longitudinal axis.

In some embodiments, the orthopaedic surgical instrument may further a housing coupled to the intramedullary rod. The housing may include a pair of arms spaced apart to define an elongated slot, and each arm may include a first longitudinal rib formed on a proximal surface and a second longitudinal rib formed on a distal surface positioned opposite the proximal surface. The frame may be configured to slide along the pair of arms. In such embodiments, the frame may comprise a first body including a central section positioned in the elongated slot of the housing and a pair of first flanges extending outwardly from the central section. Each first flange may include a proximal surface that engages the first longitudinal rib of one of the pair of arms. The frame may also comprise a second body coupled to the first body. The second body may include the base plate, the elongated shaft, and a pair of second flanges extending from the base plate transverse to the elongated shaft. Each second flange may include a distal surface that engages the second longitudinal rib of one of the pair of arms to couple the first body and the second body to the housing. The elongated shaft of the second body may extend outwardly from the base plate through the central section of the first body.

BRIEF DESCRIPTION OF THE DRAWINGS

The detailed description particularly refers to the following figures, in which:

FIG. 9 is an exploded perspective view of components of a varus/valgus adjustment mechanism of the orthopaedic surgical instrument of FIG. 1;

FIG. 10 is a perspective view of the components of FIG. 9 assembled;

DETAILED DESCRIPTION OF THE DRAWINGS

Figure 1:
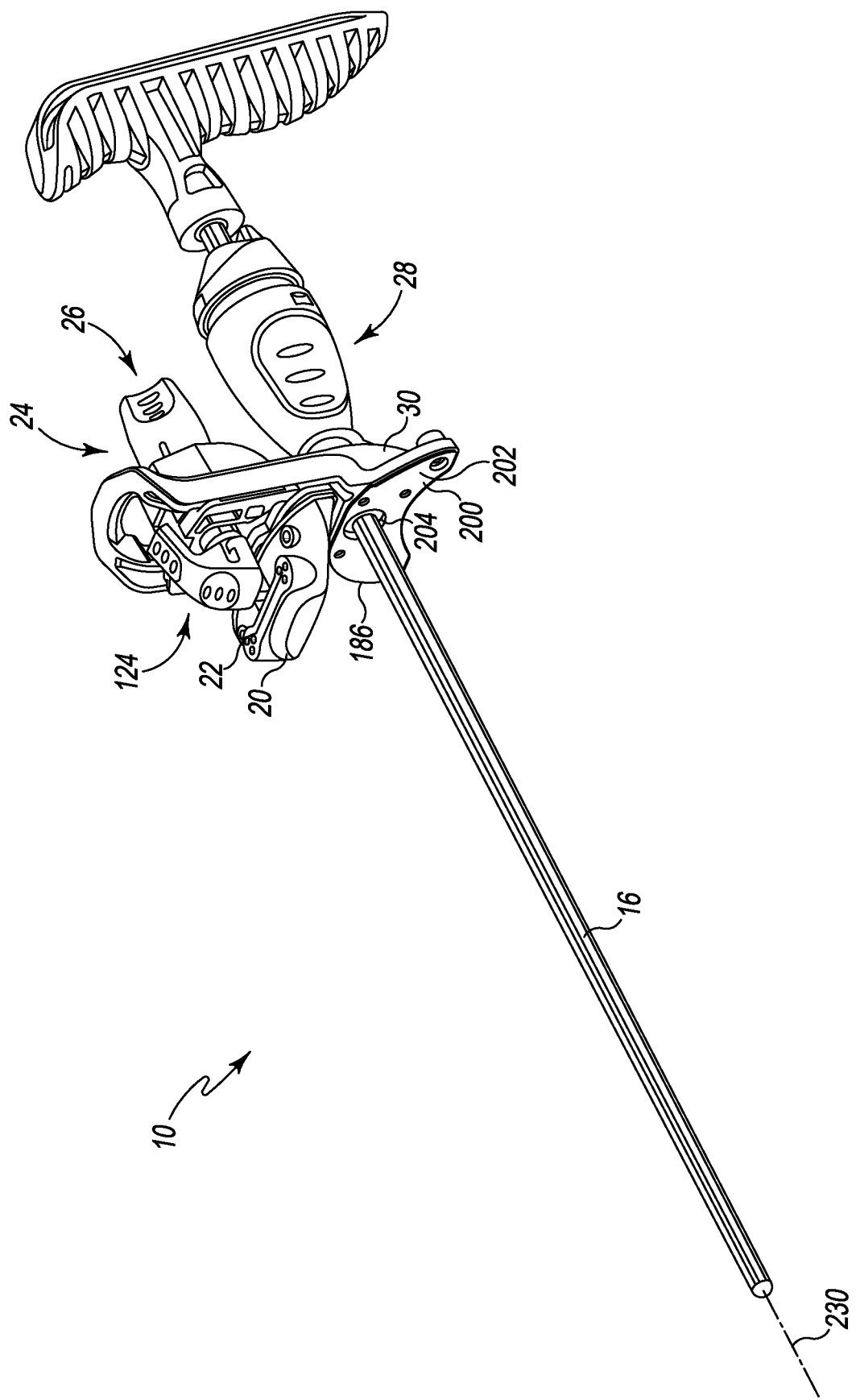
FIG. 1 is a perspective view of an orthopaedic surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 17:
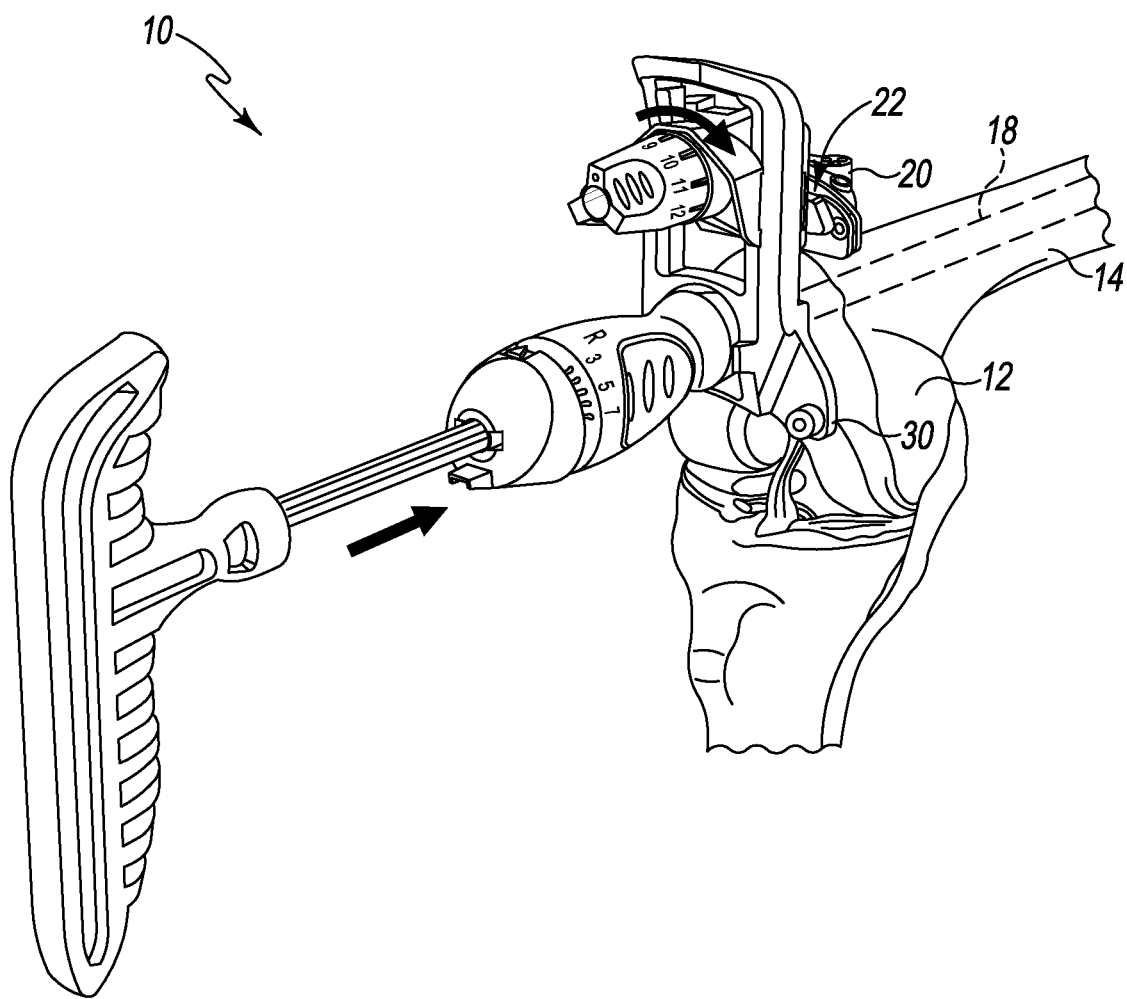
FIG. 17 is a perspective view of the orthopaedic surgical instrument of FIG. 1 positioned relative to a distal end of a patient's femur.

Referring now to FIG. 1, an orthopaedic surgical instrument 10 for use in resecting a distal end 12 of a patient's femur 14 (see FIG. 17) is shown. The instrument 10 includes an intramedullary rod 16 configured to be inserted into a medullary canal 18 of the patient's femur 14 and a cutting block 20 to guide the resection of the distal end 12. The cutting block 20 includes a cutting slot 22 that is sized to receive a cutting tool (not shown) to guide the resection. The instrument 10 includes a translation mechanism 24 operable to adjust the anterior-posterior position of the cutting block 20 relative to the distal end 12 of the patient's femur and a height adjustment mechanism 26 that is operable to adjust the depth of the resection by changing the distal-proximal distance between the cutting slot 22 and the distal end 12 of the patient's femur 14. The instrument 10 also includes a varus/valgus adjustment mechanism 28 that is operable to change the angle between the cutting slot 22 and the intramedullary rod 16 (and hence the medullary canal 18).

Referring now to FIGS. 2-5, the instrument 10 also includes a housing 30 coupled to the intramedullary rod 16. The housing 30 includes a base 32 and a pair of arms 34 that are spaced apart to define an elongated slot 36. Each arm 34 includes a longitudinal rib 38 formed on a proximal surface 40 of the arm 34. Each arm 34 also includes another longitudinal rib 42 formed on a distal surface 44 positioned opposite the proximal surface 40.

Figure 4:
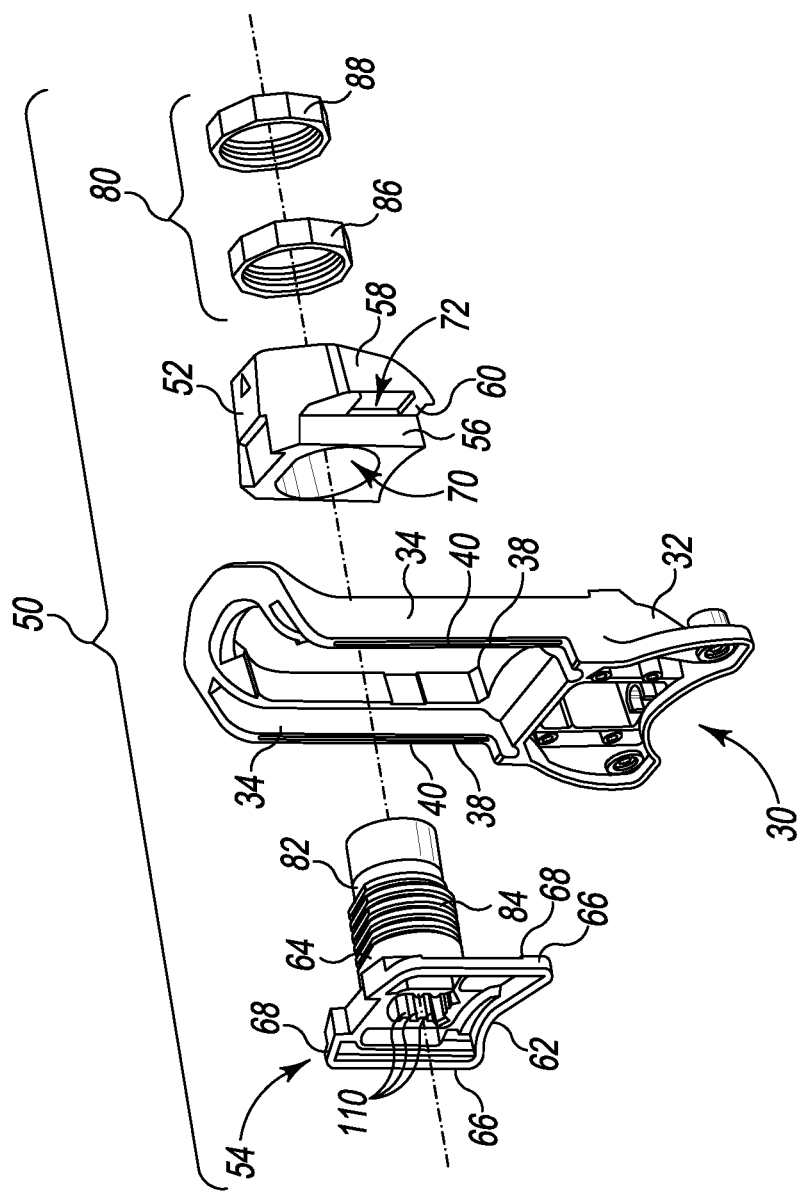
FIG. 4 is an exploded perspective view of components of a translation mechanism of the orthopaedic surgical instrument of FIG. 1.
Figure 4A:
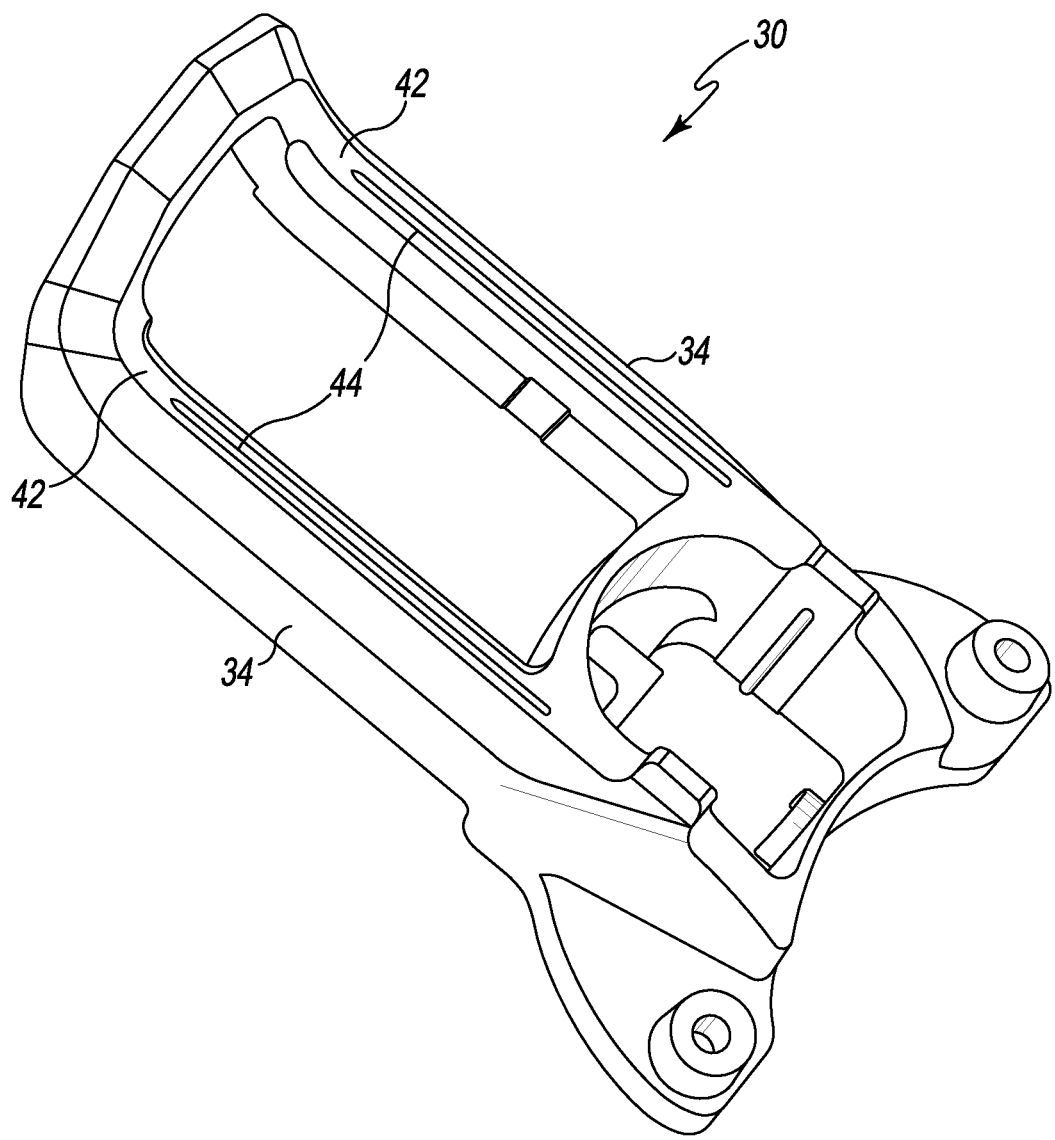
FIGS. 4A-B are perspective views of the housing of the orthopaedic surgical instrument of FIG. 1.
Figure 4B:
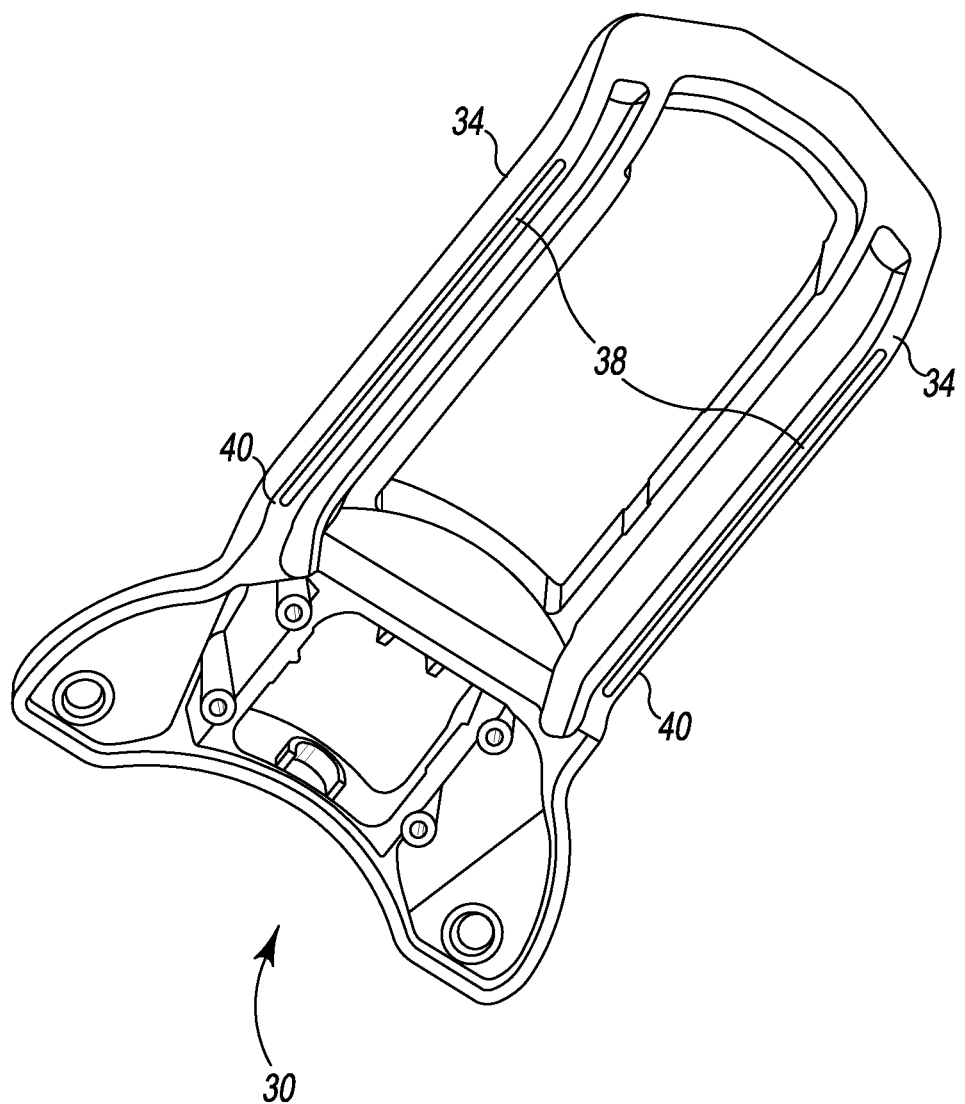

As shown in FIG. 4, the translation mechanism 24 of the instrument 10 includes a frame 50 that is configured to slide along the pair of arms 34. The frame 50 includes a distal body 52 that is coupled to the proximal body 54. The distal body 52 includes a central section 56 positioned in the elongated slot 36 of the housing 30 and a pair of flanges 58 extending outwardly from the central section 56. Each flange 58 includes a proximal surface 60 that engages the longitudinal rib 42 of one of the arms 34.

The proximal body 54 of the frame 50 includes a base plate 62 and an elongated shaft 64 that extends outwardly from the base plate 62. A pair of flanges 66 extend from the base plate 62 transverse to the elongated shaft 64. Each flange 66 includes a distal surface 68 that engages the longitudinal rib 38 of one of the pair of arms 34 to couple the distal body 52 and the proximal body 54 to the housing 30. The elongated shaft 64 of the proximal body 54 extends outwardly from the base plate 62 through a bore 70 defined in the central section 56 of the distal body 52.

Figure 2:
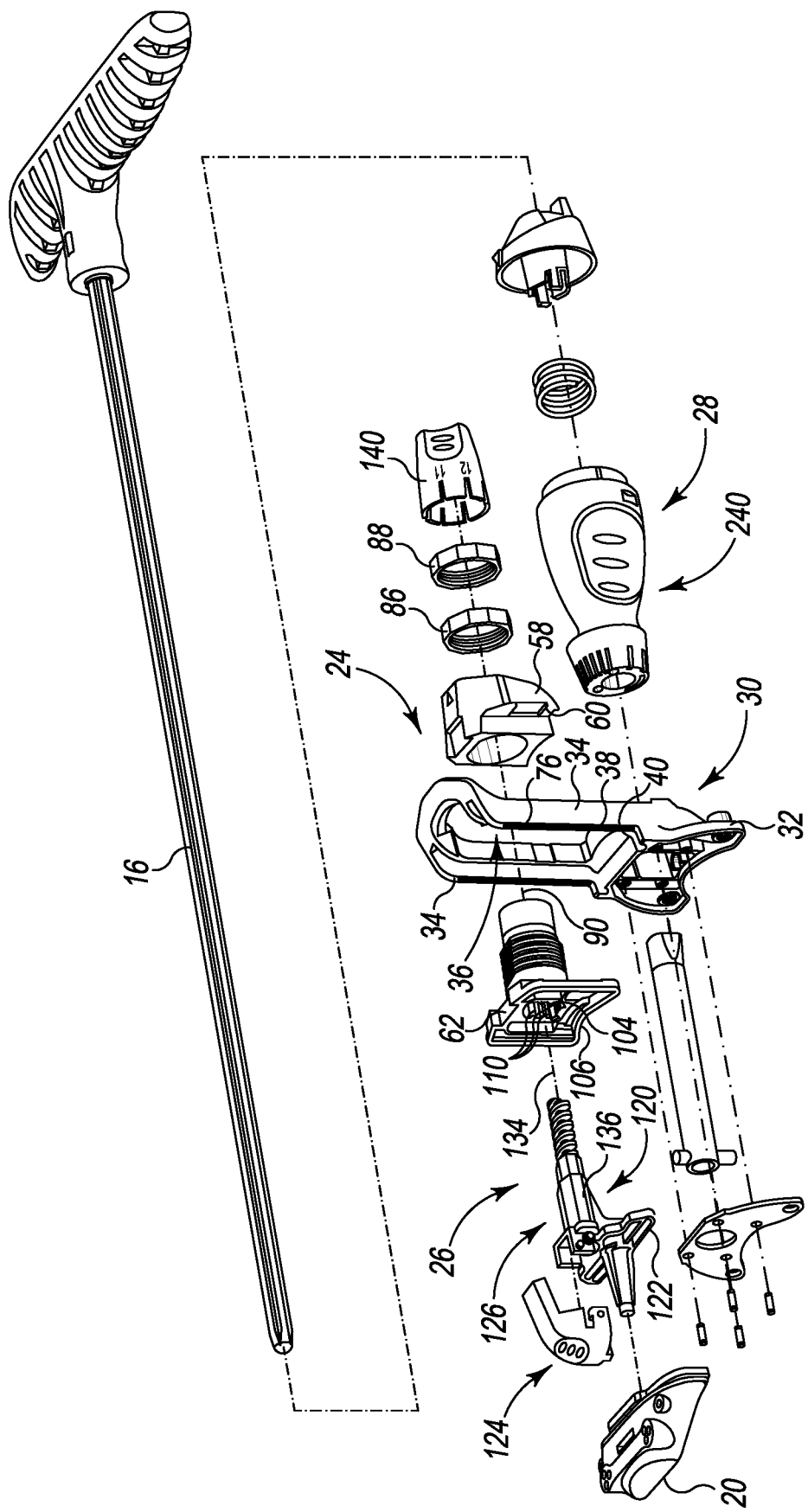
FIG. 2 is an exploded perspective view of the orthopaedic surgical instrument of FIG. 1.
Figure 3:
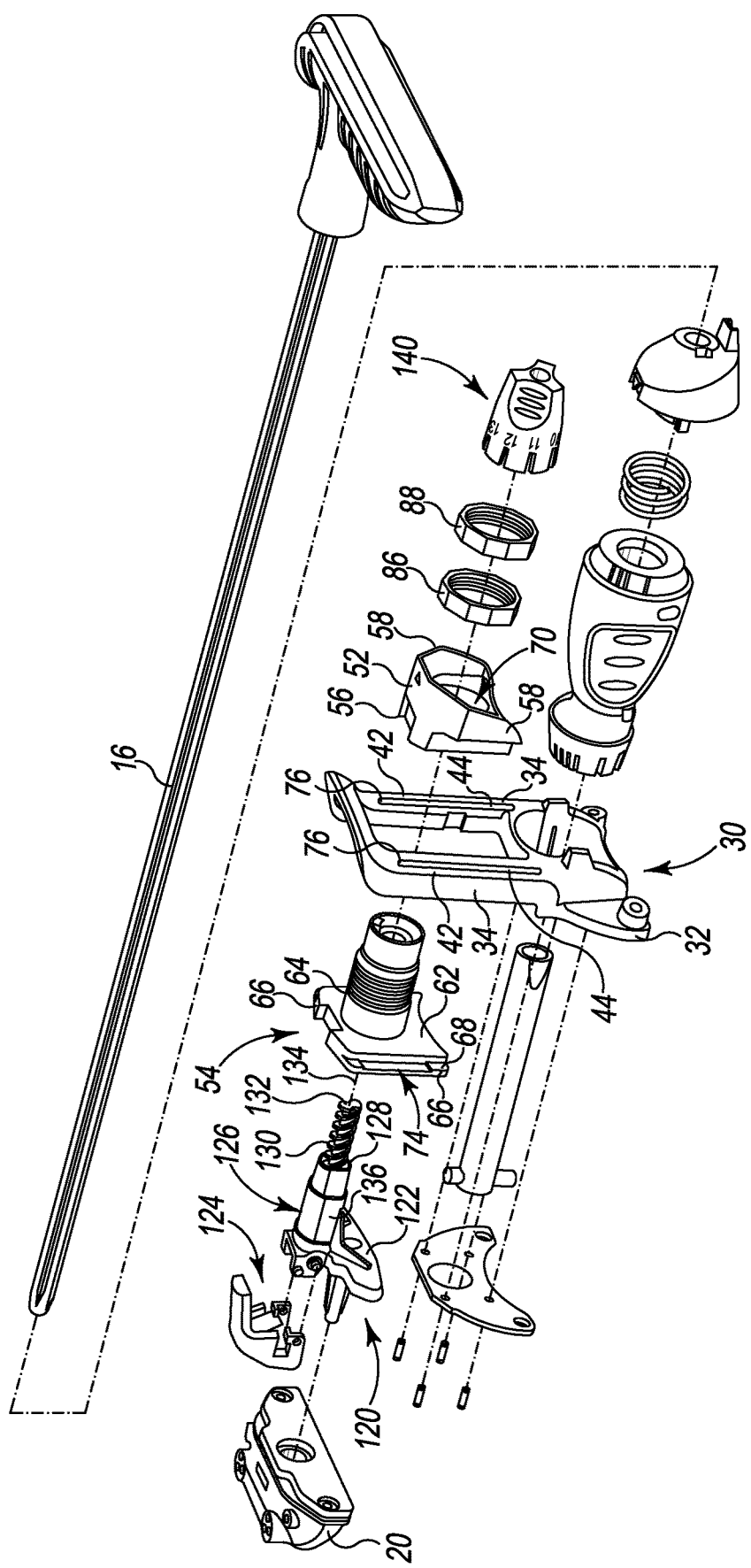
FIG. 3 is another exploded perspective view taken from another angle of the orthopaedic surgical instrument of FIG. 1.
Figure 5:
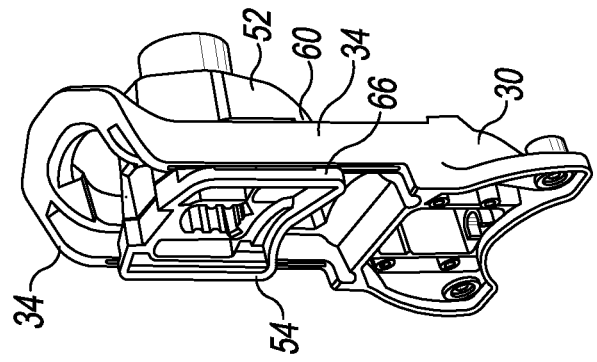
FIG. 5 is a perspective view of the assembled components of FIG. 4.

As shown in FIG. 4, a pocket 72 is defined in the proximal surface 60 of each flange 58 to create a relief section in the proximal surface 60. As shown in FIG. 3, a pocket 74 is defined in the distal surface 68 of each flange 66 to create a relief section in the distal surface 68. As shown in FIGS. 2 and 3, each of the longitudinal ribs 38, 42 includes curved outer surface 76 that engages the proximal surface 60 and the distal surface 68 of the flanges 58, 66.

Returning to FIG. 4, the frame 50 also includes a fastener 80 secured to the elongated shaft 64 of the proximal body 54 to couple the bodies 52, 54 together and clamp the arms 34 between the bodies 52, 54. The elongated shaft 64 has an outer surface 82 that includes a threaded section 84 configured to receive the fastener 80. The fastener 80 includes a locking ring 86 that is threaded onto the threaded section 84 of the elongated shaft 64. The fastener 80 also includes another locking ring 88 that is threaded onto the elongated shaft 64 to retain the locking ring 86 in position on the elongated shaft 64.

Figure 6:
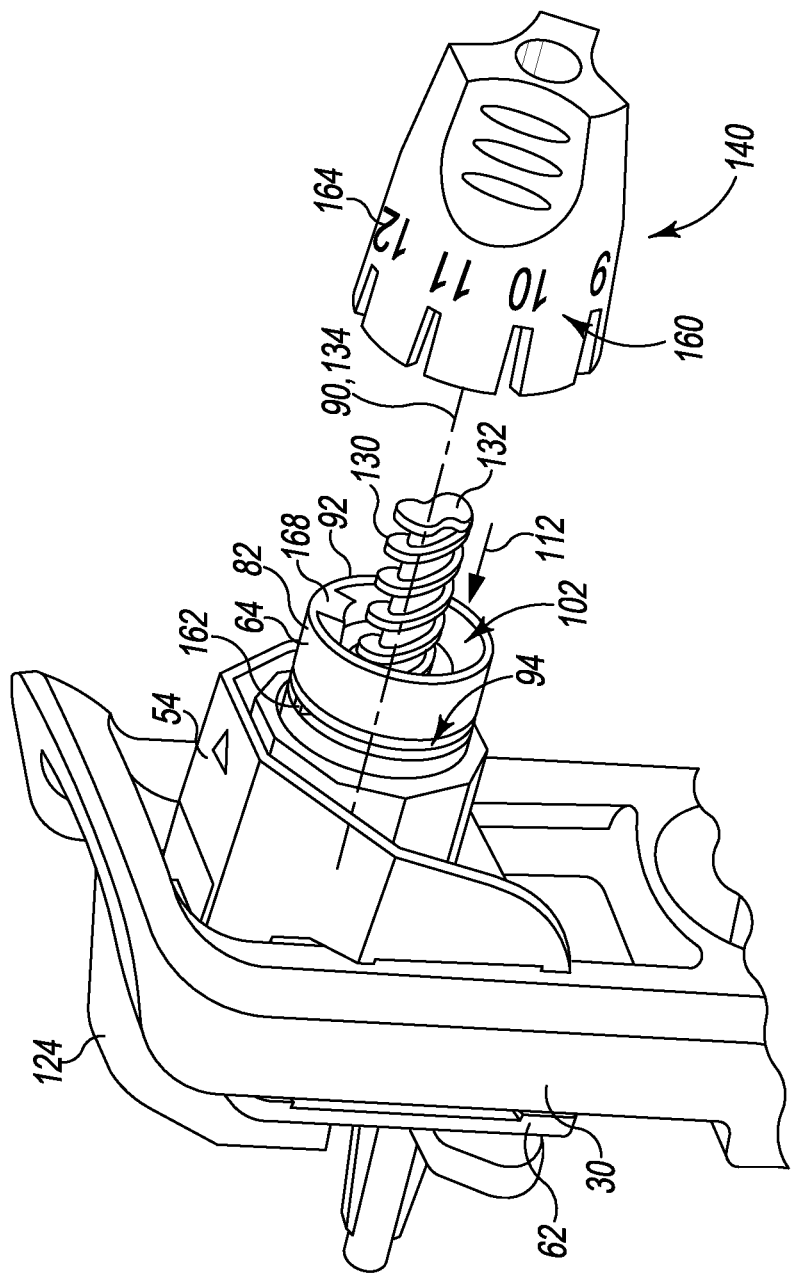
FIG. 6 is exploded perspective view of components of a height adjustment mechanism of the orthopaedic surgical instrument of FIG. 1.
Figure 7:
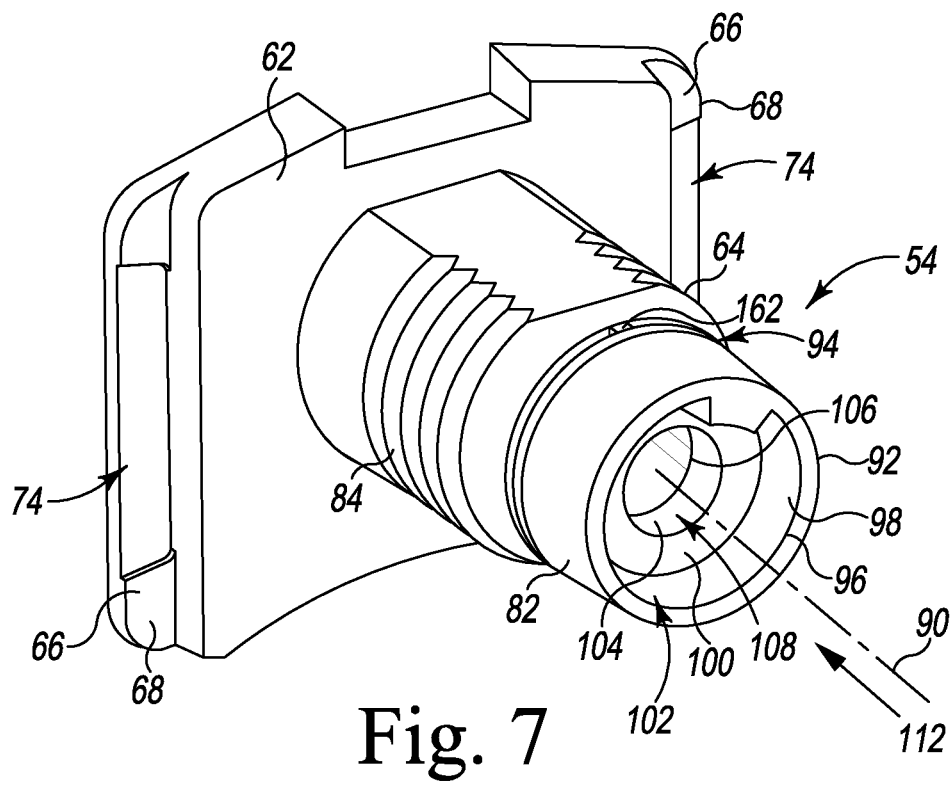
FIG. 7 is a perspective view of a component of the height adjustment mechanism of the orthopaedic surgical instrument of FIG. 1.
Figure 7A:
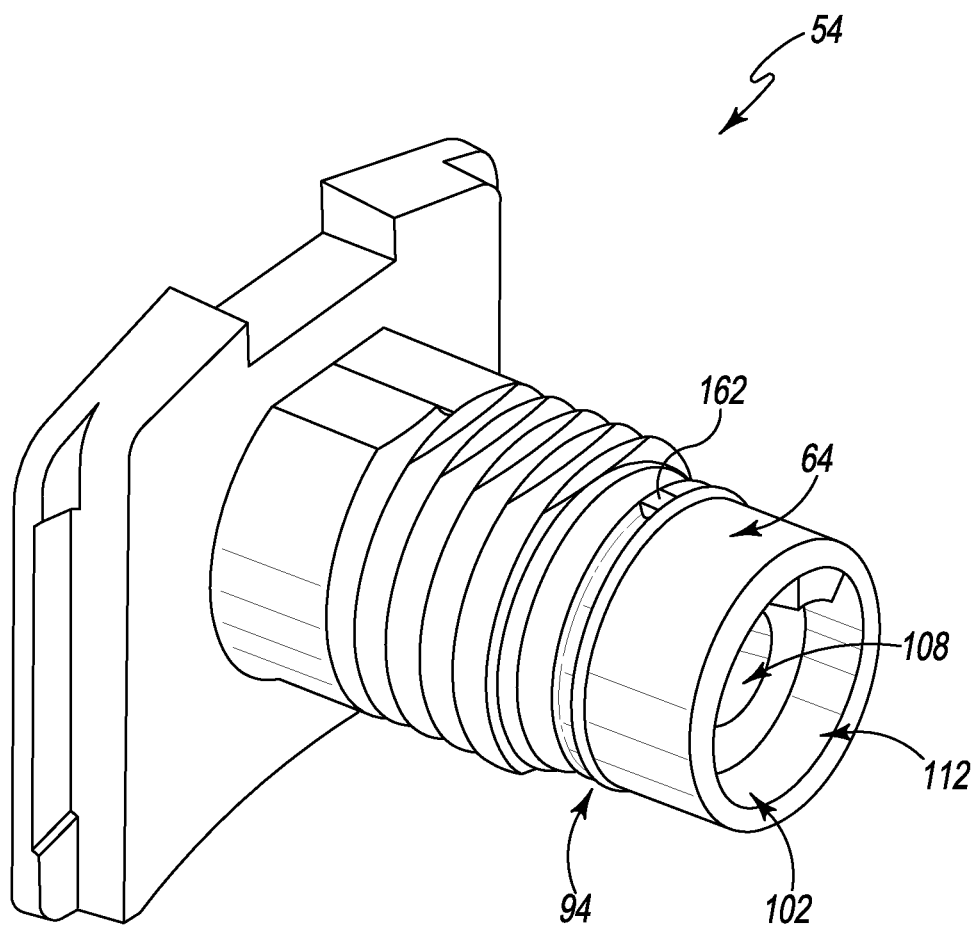
FIG. 7A is another perspective view of the component of FIG. 7.
Figure 7B:
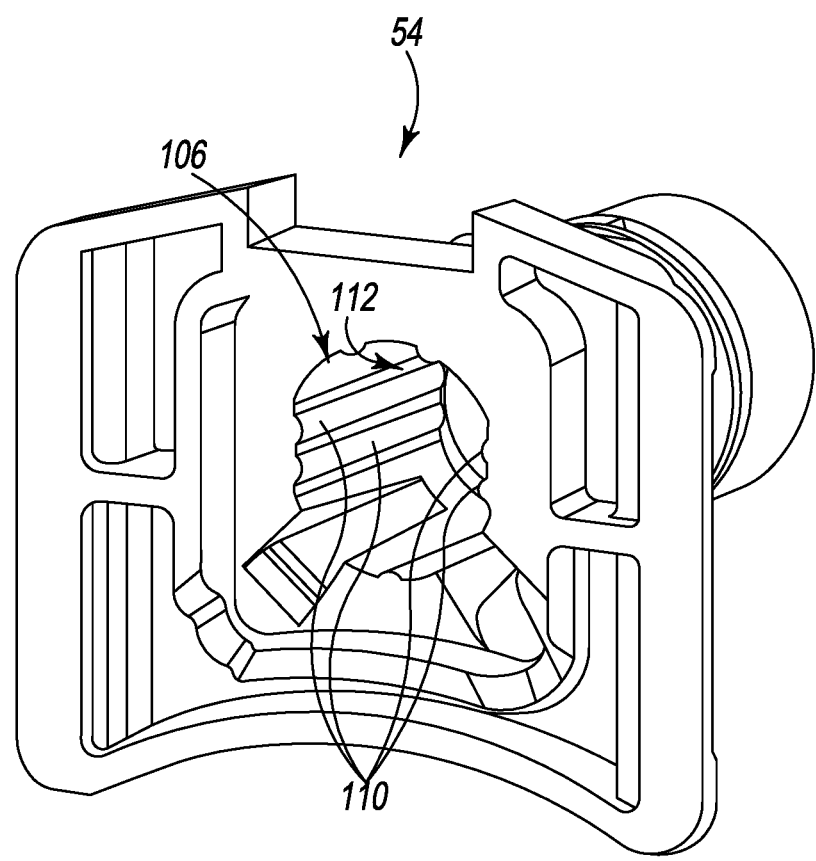
FIG. 7B is a proximal perspective view of the component of FIG. 7.
Figure 8A:
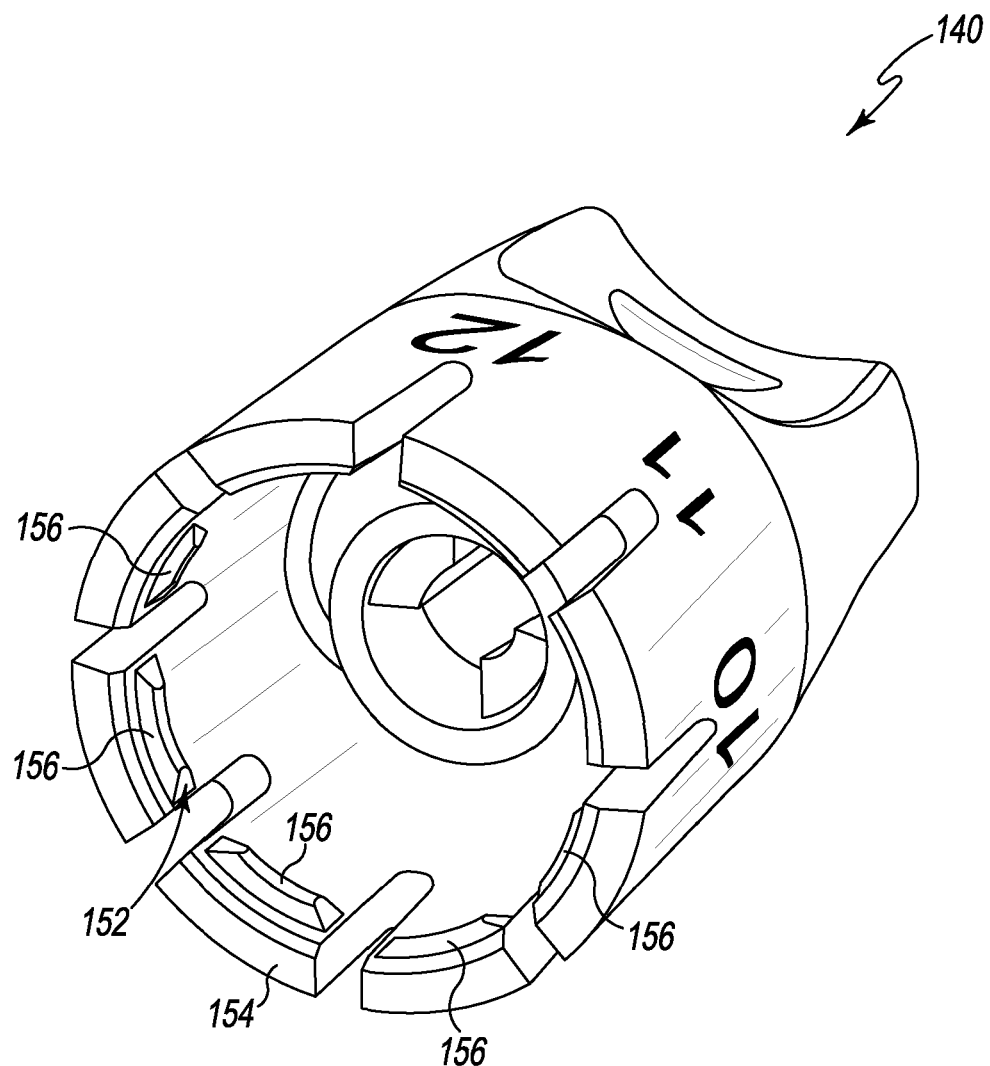
FIG. 8A another perspective view of the control knob of FIG. 8.

As shown in FIGS. 6-7, the elongated shaft 64 of the proximal frame body 54 extends along a longitudinal axis 90 to a distal end 92. An annular groove 94 is formed on the outer surface 82 of the elongated shaft between the distal end 92 and the threaded section 84. As shown in FIG. 7, an opening 96 is defined in the distal end 92, and an inner wall 98 extends inwardly from the opening 96 to a rim wall 100. The inner wall 98 and the rim wall 100 cooperate to define an aperture 102 in the distal end. As shown in FIGS. 2 and 7, the proximal frame body 54 also includes an inner wall 104 that extends inwardly from the rim wall 100 to an opening 106 defined in the base plate 62. The inner wall 104 defines a bore 108 in the proximal frame body 54, and, as shown in FIG. 7A, the bore 108 and the aperture 102 cooperate to define a passageway 112 that extends through the proximal frame body 54. As shown in FIG. 7B, a plurality of ribs 110 are formed on the inner wall 104, which engage a mounting bracket 120 of the height adjustment mechanism 26, as described in greater detail below.

As described above, the height adjustment mechanism 26 is operable to adjust the depth of the resection by changing the distal-proximal distance between the cutting slot 22 and the distal end 12 of the patient's femur 14. Returning to FIG. 2, the mounting bracket 120 includes a main body 122 that is positioned on the proximal side of the base plate 62 of the proximal frame body 54. As shown in FIGS. 2-3, the main body 122 includes a locking mechanism 124 configured to secure the cutting block 20 to the mounting bracket 120. In the illustrative embodiment, the locking mechanism 124 is operable to attach and detach the cutting block 20 from the mounting bracket 120.

The mounting bracket 120 also includes an elongated body 126 that extends outwardly from the main body 122 to a distal end 128. A threaded helix rod 130 extends outwardly from the distal end 128 to a distal tip 132. The elongated body 126 and the threaded rod 130 extend along a longitudinal axis 134 that extends through the distal tip 132. The elongated body 126 also includes a pair of planar surfaces 136 that engage the plurality of ribs 110 of the proximal frame body 54 to prevent rotation of the mounting bracket 120 about the longitudinal axis 134.

As shown in FIG. 6, the threaded rod 130 of the mounting bracket 120 extends outwardly along the longitudinal axis 134 from the passageway 112 defined in the proximal frame body 54. The height adjustment mechanism 26 includes a control knob 140 that is positioned over the distal tip 132 of the threaded rod 130 of the mounting bracket 120. In the illustrative embodiment, the control knob 140 is rotatable about the longitudinal axis 134 to adjust an adjustment (i.e., distal-proximal) distance between the cutting slot 22 of the cutting block 20 and the base plate 62 of the frame 50 and hence adjust the depth of the resection.

Figure 8:
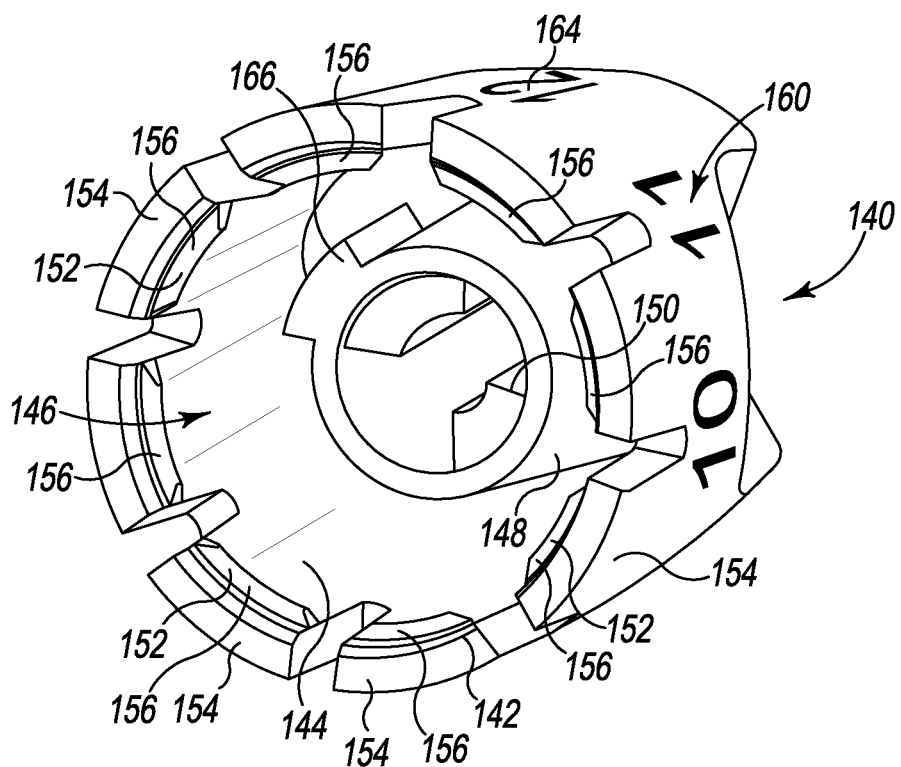
FIG. 8 is a perspective view of a control knob of the height adjustment mechanism of the orthopaedic surgical instrument of FIG. 1.

As shown in FIG. 8, the control knob 140 includes a proximal opening 142. An inner wall 144 extends inwardly from the opening to define an aperture 146 in the control knob 140, which receives the threaded rod 130. A hub 148 is positioned in the aperture 146, and the hub 148 has a threaded inner surface (formed by tabs 150) that engages the threaded rod 130 to couple the mounting bracket to the control knob. The control knob 140 also includes an annular rib 152 that is formed on the inner wall 144. The annular rib 152 engages the annular groove 94 formed on the elongated shaft 64 of the frame 50 to secure the control knob 140 and the mounting bracket 120 to the frame 50, and hence secure the height adjustment mechanism 26 to the translation mechanism 24 of the instrument 10. In the illustrative embodiment, the annular rib 152 of the control knob 140 is formed on a plurality of cantilevered arms 154 of the control knob 140. As shown in FIG. 8, the annular rib 152 is divided into rib portions 156, with one rib portion 156 formed on each cantilevered arms 154 of the control knob 140.

As shown in FIG. 6, the control knob 140 includes a plurality of visual indicators 160 corresponding to a plurality of different adjustment distances. The frame 50 includes an alignment guide 162 configured to be aligned with a first visual indicator 164 of the plurality of visual indicators 160 of the control knob 140 to index the control knob to a first adjustment distance. In the illustrative embodiment, the alignment guide 162 is a tab 162 formed in (and extending outwardly from) the annular groove 94 formed on the elongated shaft 64 of the frame 50.

In use, when the control knob 140 is rotated about the axis 134, the threaded rod 130 is driven in a proximal-distal direction relative to the frame 50 to change the position of the cutting block 20 relative to the frame 50. As the control knob 140 is rotated, the annular rib portions 156 on the cantilevered arms 154 are advanced into engagement with the tab 162 formed in the annular groove 94 of the elongated shaft 64. Each cantilevered arm 154 is deflected outward slightly such that each rib portion 156 is permitted to drive over the tab 162 before dropping into the next distance setting. The control knob 140 and the elongated shaft 64 of the frame 50 include features to prevent the control knob 140 from rotating 360 degrees about the axis 134. As shown in FIG. 8, the control knob 140 includes a tab 166 that extends outwardly from the hub 148. The tab 166 is configured to engage another tab 168 (see FIG. 6) positioned in the aperture 102 of the elongated shaft 64 of the frame 50. In the illustrative embodiment, the tabs 166, 168 engage one another at a first rotational position of the control knob 140 corresponding to the minimum adjustment distance of the cutting block 20 and at a second rotational position of the control knob 140 corresponding to the maximum adjustment distance of the cutting block 20. An angle is defined about the axis 134 between the first rotational position and the second rotational position. The angle defines the maximum rotation of the control knob 140 about the longitudinal axis 134.

Figure 13:
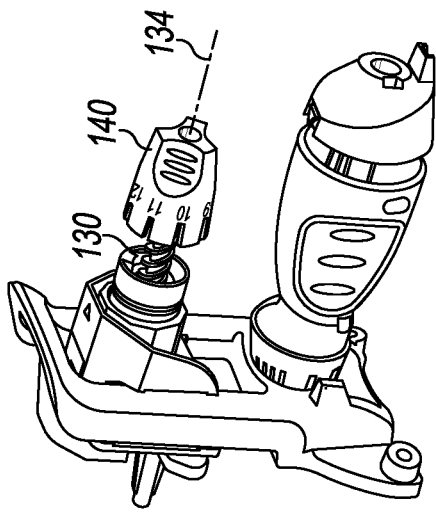
FIGS. 12-15 are perspective views of the orthopaedic surgical instrument of FIG. 1 at various stages of assembly.
Figure 15:
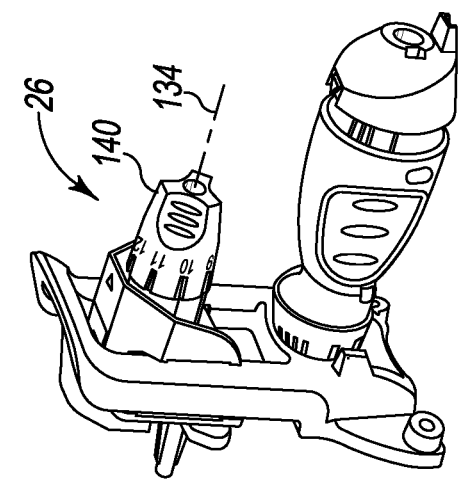
Figure 12:
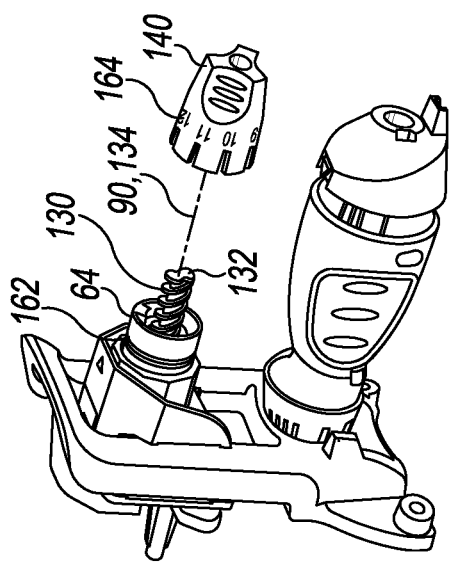
Figure 14:
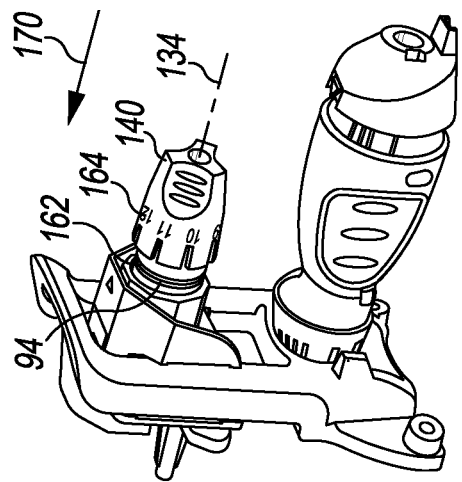

The steps for assembling the control knob 140 on the mounting bracket 120 and the translation frame 50 are shown in FIGS. 12-15. As shown in FIG. 12, the control knob 140 is aligned with the distal tip 132 of the threaded rod 130, which extends outwardly from the elongated shaft 64 of the translation frame. The control knob 140 is rotated to align the visual indicator 164 with the alignment guide 162 on the outer surface of the elongated shaft 64. The control knob 140 may be then advanced over the distal tip 132 of the threaded rod 130, as shown in FIG. 13. The knob 140 may be rotated about the axis 134 to engage the tabs 150 of the knob hub 148 with the threaded rod 130. When the visual indicator 164 is again aligned with the alignment guide 162, as shown in FIG. 14, the knob 140 may be advanced axially in the direction indicated by arrow 170 to advance the arms 154 of the control knob 140 over the annular groove 94 of the elongated shaft 64 to secure the control knob 140 to the translation frame 50.

The translation mechanism 24 and the height adjustment mechanism 26 are mounted on a housing 30 coupled to the intramedullary rod 16. As shown in FIG. 9, the housing 30 includes a base 32 and a central slot 180 that is spaced apart from the elongated slot 36 and is defined in the base 32. A pair of brackets 182 are formed on opposite anterior/posterior walls 184 that define the central slot 180. As described in greater detail below, an elongated tube 186 of the varus/valgus adjustment mechanism 28 is mounted to the housing 30 via the brackets 182.

As described above, the varus/valgus adjustment mechanism 28 of the instrument 10 is operable to change the angle between the cutting slot 22 and the intramedullary rod 16 (and hence the medullary canal 18). The adjustment mechanism 28 includes the elongated tube 186 that extends from a proximal end 188 that is positioned in the central slot 180 of the housing 30 to a distal end 190. A pair of pivot pins 192 are coupled to the proximal end 188 of the elongated tube 186, and each pin 192 is positioned in one of the brackets 182. The pins 192 cooperate to define a pivot axis 194 of the varus/valgus adjustment mechanism 28.

The instrument 10 also includes a distal plate 200 that is coupled to the housing 30. In the illustrative embodiment, the distal plate 200 is formed from a metallic material. The plate 200 includes a bone-engaging surface 202 and an opening 204 that is defined in the bone-engaging surface 202. As shown in FIG. 9, the opening 204 is aligned with the central slot 180 of the housing 30 and the proximal end 188 of the elongated tube 186.

Figure 11:
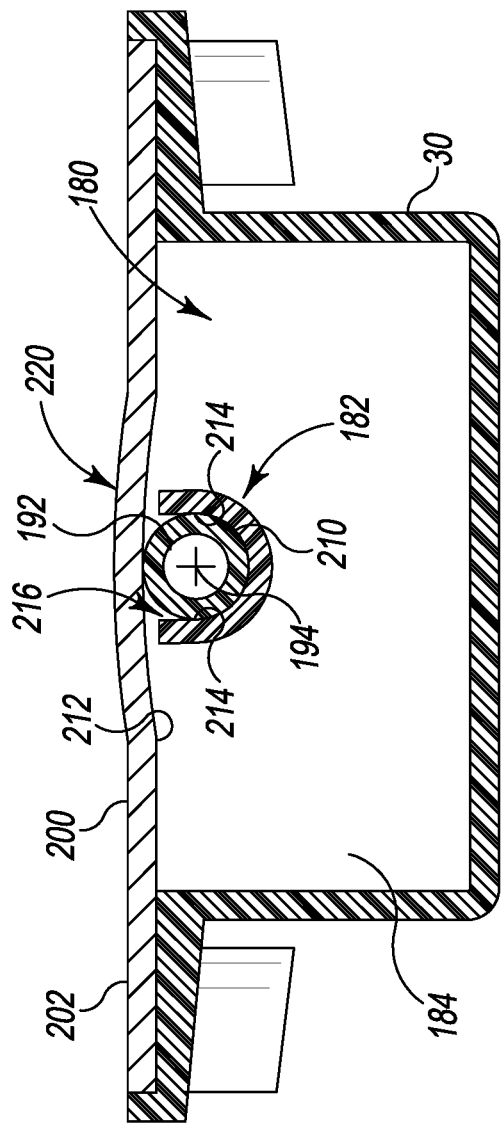
FIG. 11 is a cross-sectional elevation view taken along the line 11-11 in FIG. 10.

As shown in FIG. 10, the plate 200 is secured to the housing 30 via a plurality of fasteners 206 that extend through the plate 200 into mounting holes 208 defined in the housing 30 to clamp the pivot pins 192 between inner walls of the brackets 182 and the distal plate 200. As shown in FIG. 11, the brackets 182 include distal-facing inner walls 210, and the plate 200 includes a proximal-facing surface 212. The pivot pins are clamped between distal-facing inner walls of the brackets and a proximal-facing surface of the distal plate in the illustrative embodiment.

Each bracket 182 also includes a pair of side inner walls 214 that cooperate with the distal-facing inner wall 210 to define an open-ended channel 216 that receives a pivot pin 192. In the illustrative embodiment, each pivot pin 192 sits proud in its bracket 182, i.e., each pin 192 extends outwardly from the open-ended channel of its corresponding bracket. The distal plate 200 engages the pivot pins 192 to retain the pivot pins 192 in the brackets 182. As shown in FIG. 11, the distal plate 200 includes a bowed central section 220 that engages the pivot pins 192 such that the pivot pins 192 are clamped with sufficient force to retain them in the brackets 182 but also to permit the pins 192 to pivot about axis 194.

Figure 16:
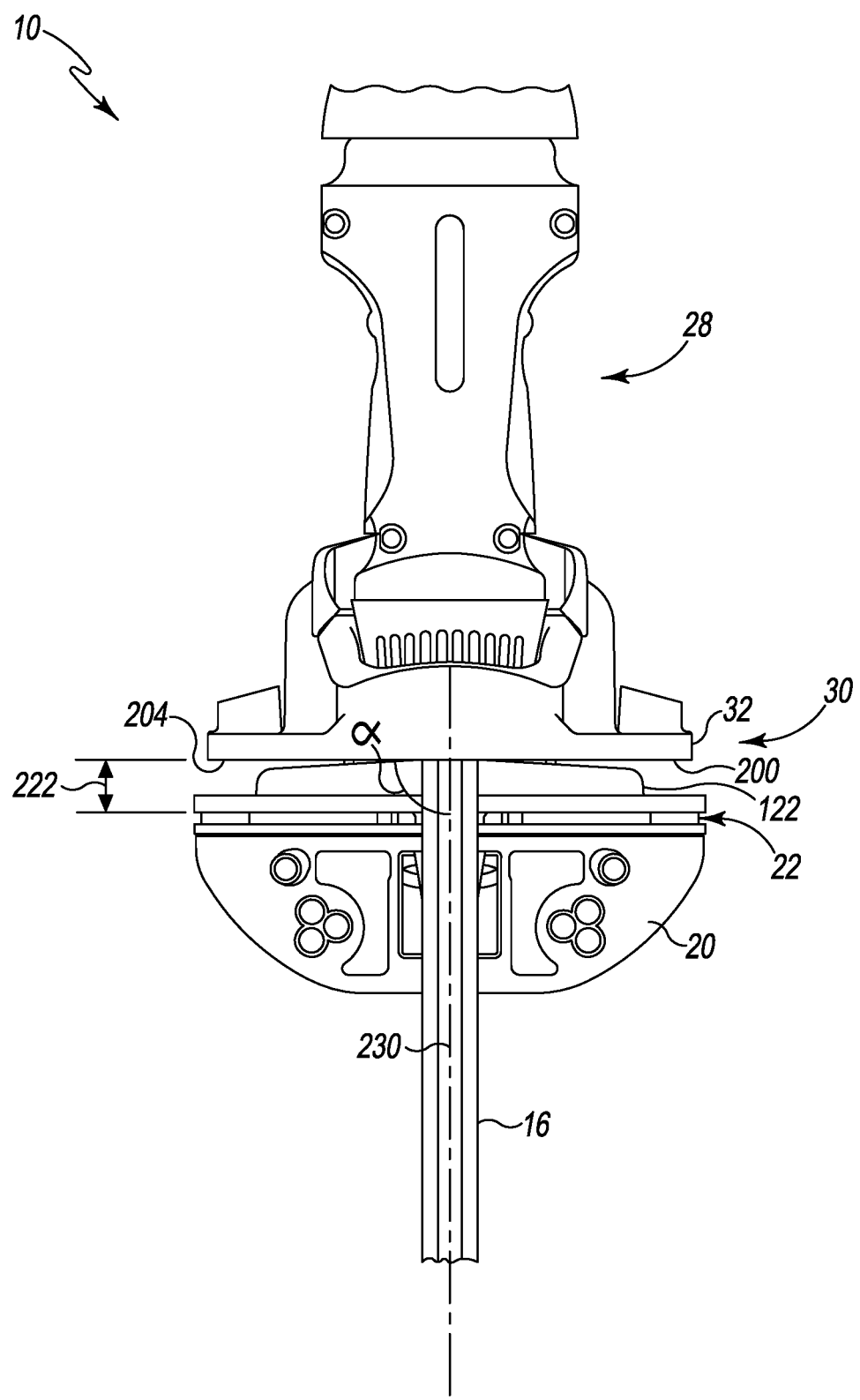
FIG. 16 is a rear elevation view of the orthopaedic surgical instrument of FIG. 1.

It should be understood that the relative proximal-distal height between the bone-engaging surface 202 of the distal plate 200 and the base plate 62 of the translation mechanism 24 are fixed. Additionally, the bone-engaging surface 202 of the plate 200 extends generally parallel to the cutting slot 22 of the cutting block 20. As a result, when the height adjustment mechanism 26 is operated to adjust the position of the cutting block 20 relative to the base plate 62, the relative proximal-distal distance 222 (see FIG. 16) between the cutting slot 22 of the cutting block 20 and the bone-engaging surface 202 of the distal plate 200 (and hence the distal end 12 of the patient's bone) is also thereby adjusted.

Returning to FIG. 1, the intramedullary rod 16 of the instrument 10 extends through the elongated tube 186 and the opening 204 defined in the distal plate 200. A longitudinal axis 230 is defined by the intramedullary rod 16, which extends transverse to the bone-engaging surface 202 of the distal plate 200. As described above, the pivot pins 192 cooperate to define a pivot axis 194 about which the elongated tube 186 and the intramedullary rod 16 are configured to pivot relative to the distal plate 200 to change a magnitude of an angle α defined between the longitudinal axis 230 and the bone-engaging surface 202 of the distal plate 200 (see FIG. 16).

The varus/valgus adjustment mechanism 28 includes an adjustment device 240 that is positioned over the distal end 190 of the elongated tube 186 and coupled to the housing 30. An exemplary adjustment device 240 is shown and described in U.S. Patent App. Pub. No. 2013/0317501, which is expressly incorporated herein by reference.

In the illustrative embodiment, the elongated tube 186, pivot pins 192, and housing 30 are plastic components. The components of the frame 50 of the translation mechanism 24 are also formed from plastic. The main body 122 and the elongated body 126 of the mounting bracket 120 are also formed from plastic. The cutting block 20 is formed as a plastic component with a metallic insert defining the cutting slot 22.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument, comprising:
   a cutting block including a cutting slot sized to receive a cutting tool to guide a resection of distal end of a patient's femur, a housing coupled to the cutting block, the housing including a central slot and a pair of brackets positioned on opposite sides of the central slot, a distal plate coupled to the housing, the distal plate including a bone-engaging surface extending between an anterior end and a posterior end of the distal plate and an opening that is defined in the bone-engaging surface at a location between the anterior end and the posterior end of the distal plate and is aligned with the central slot, an elongated shaft extending from a first end positioned in the central slot, a pair of pivot pins coupled to the elongated shaft, each pivot pin being positioned in one of the pair of brackets, and an intramedullary rod configured to be inserted into a medullary canal of the patient's femur, the intramedullary rod extending through the elongated shaft and the opening defined in the distal plate and defining a longitudinal axis that extends transverse to the bone-engaging surface of the distal plate, wherein the bone-engaging surface extends generally parallel to the cutting slot of the cutting block, wherein the pivot pins cooperate to define a pivot axis about which the elongated shaft and the intramedullary rod are configured to pivot relative to the distal plate to change a magnitude of an angle defined between the longitudinal axis and the bone-engaging surface of the distal plate, and wherein the distal plate engages the pivot pins to retain the pivot pins in the brackets of the housing.

2. The orthopaedic surgical instrument of claim 1, wherein the distal plate is formed from a metallic material, and the pivot pins are formed from a plastic material.

3. The orthopaedic surgical instrument of claim 1, further comprising at least one fastener that secures the distal plate to the housing to clamp the pivot pins between inner walls of the brackets and the distal plate.

4. The orthopaedic surgical instrument of claim 1, wherein the pivot pins are clamped between distal-facing inner walls of the brackets and a proximal-facing surface of the distal plate.

5. The orthopaedic surgical instrument of claim 4, wherein:

each bracket includes the distal-facing inner wall and a pair of side inner walls that cooperate with the distal-facing inner wall to define an open-ended channel sized to receive one of the pivot pins, and each pivot pin extends outwardly from the open-ended channel of its corresponding bracket.

6. The orthopaedic surgical instrument of claim 5, wherein the distal plate includes a bowed central section that engages the pivot pins extending outwardly from the open-ended channels of the brackets.

* * * * *